US009741110B2

(12) United States Patent
Hata et al.

(10) Patent No.: US 9,741,110 B2
(45) Date of Patent: Aug. 22, 2017

(54) CELL CULTURE EVALUATION SYSTEM FOR MEASURING SUSPENSION CELLS, CELL CULTURE EVALUATION METHOD FOR MEASURING SUSPENSION CELLS, AND CELL CULTURE EVALUATION PROGRAM FOR MEASURING SUSPENSION CELLS

(75) Inventors: Norihiko Hata, Yokohama (JP); Hidemasa Jinguji, Yokohama (JP)

(73) Assignee: MEDINET CO., LTD. (JP)

( * ) Notice: Subject to any disclaimer, the term of this patent is extended or adjusted under 35 U.S.C. 154(b) by 1923 days.

(21) Appl. No.: 11/886,943

(22) PCT Filed: Mar. 17, 2006

(86) PCT No.: PCT/JP2006/305464
§ 371 (c)(1),
(2), (4) Date: Dec. 6, 2007

(87) PCT Pub. No.: WO2006/101056
PCT Pub. Date: Sep. 28, 2006

(65) Prior Publication Data
US 2008/0201083 A1    Aug. 21, 2008

(30) Foreign Application Priority Data
Mar. 22, 2005   (JP) .................................. 2005-82763

(51) Int. Cl.
*G01N 33/48*    (2006.01)
*G06T 7/00*     (2017.01)
(Continued)

(52) U.S. Cl.
CPC .......... *G06T 7/0012* (2013.01); *C12M 41/36* (2013.01); *G06K 9/00147* (2013.01); *G06T 2207/30024* (2013.01)

(58) Field of Classification Search
CPC ........ G06T 7/0012; G06T 2207/30024; C12M 41/36; C12M 23/58; C12M 41/48; C12M 41/46; C12M 41/14; G06K 9/00147
(Continued)

(56) References Cited

U.S. PATENT DOCUMENTS 5,487,112 A * 1/1996 Zygourakis et al. ......... 382/133
6,008,010 A * 12/1999 Greenberger et al. ......... 435/41
(Continued)

FOREIGN PATENT DOCUMENTS

JP    2001-224366 A    8/2001
JP    2001-275659 A    10/2001
(Continued)

OTHER PUBLICATIONS

Jozsef Baranyi; Stochastic modelling of bacterial lag phase; International Journal of Food Microbiology 73 (2002) p. 203-206.*
(Continued)

*Primary Examiner* — William H Beisner
*Assistant Examiner* — Danielle Henkel
(74) *Attorney, Agent, or Firm* — Harness, Dickey & Pierce, P.L.C.

(57) ABSTRACT

There is provided a cell culture evaluation system, a cell culture evaluation method, and a cell culture evaluation program which are capable of estimating and evaluating the lag time or the minimum doubling time and objectively and adequately determining whether or not a cell population is stimulated for proliferation by using an average projected area of a cultured cell population or the rate of increasing the ratio of the non-single-cells as an evaluation parameter when culturing the cells. Images of the cell population to be cultured statically are acquired in a culture vessel, the average projected areas of the cells are calculated from the images for the respective culture times, and the lag times at
(Continued)

lag phase are calculated from the calculated average projected areas of the cells. The single-cells and the non-single-cells are discriminated from the images, and the increasing rate of the non-single-cells is calculated from the ratio of the non-single-cells in the cell population to determine the minimum doubling time from the increasing rate of the non-single-cells. Whether or not the cell population is stimulated for proliferation is determined from the ratio of the non-single-cells.

9 Claims, 12 Drawing Sheets

(51) Int. Cl.
    *C12M 1/34*     (2006.01)
    *G06K 9/00*     (2006.01)
(58) Field of Classification Search
    USPC .................. 702/21; 435/288.7; 382/133, 134
    See application file for complete search history.

(56) References Cited

U.S. PATENT DOCUMENTS

| | | | |
|---|---|---|---|
| 2003/0054335 A1 | 3/2003 | Taya et al. | |
| 2003/0134269 A1* | 7/2003 | Hirai et al. | 435/4 |

FOREIGN PATENT DOCUMENTS

| | | |
|---|---|---|
| JP | 2002-189013 A | 7/2002 |
| JP | 2002-218995 A | 8/2002 |
| JP | 2003-021628 A | 1/2003 |
| JP | 2003-500065 A | 1/2003 |
| JP | 2004-344049 A | 12/2004 |

OTHER PUBLICATIONS

Japanese Office Action dated Sep. 2, 2011 (and English translation thereof) in counterpart Japanese Application No. 2007-509249.

Hata, Norihiko et al, "Kobetsu Saibo Kyodo Kansatsu ni Motozuku Baiyo Parameter Hyoka." The Society for Biotechnology, Japan Taikai Koen Yoshishu, Sep. 25, 2002, vol. 2002, p. 203, lecture subject No. 1120.

Kinooka, Masahiro et al, "Nanoscale Ototsumen no Sekkei to Saibo Hyoka eno Tekiyo," Dai 69 Kai, The Society of Chemical Engineers, Japan Nenkai Kenkyu Happyo Koen Yoshishu, Mar. 2, 2004, p. 722.

Extended European Search Report (EESR) dated Nov. 22, 2012 (in English) issued in counterpart European Application No. 06729453.8.

Jozsef Barnayi: "Stochastic modelling of bacterial lag phase": International Journal of Food Microbiology: 73 (2002): Mar. 11, 2002: pp. 203-206 (in English).

* cited by examiner

CELL CULTURE EVALUATION SYSTEM FOR MEASURING SUSPENSION CELLS, CELL CULTURE EVALUATION METHOD FOR MEASURING SUSPENSION CELLS, AND CELL CULTURE EVALUATION PROGRAM FOR MEASURING SUSPENSION CELLS

This application is a U.S. National Phase Application under 35 USC 371 of International Application PCT/JP2006/305464 filed Mar. 17, 2006.

TECHNICAL FIELD

The present invention relates to a cell culture evaluation system, a cell culture evaluation method, and a cell culture evaluation program, and more specifically, to a cell culture evaluation system, a cell culture evaluation method, and a cell culture evaluation program which are capable of effective estimation and evaluation of lag time and minimum doubling time in suspension cell culture, and objective and adequate determination whether or not a cell population is stimulated for proliferation.

BACKGROUND ART

In the related art, a method of evaluating proliferation potential of suspension culture is performed, for example, by sampling culture solution mixed evenly by stirring or the like or by measuring the number of living cells from the turbidity of the culture solution and estimating a proliferation profile. However, in the field of static culture of Lymphokine Activated Killer cells (hereinafter referred to as LAK cells) used, for example, for immune cell therapy, the cells are adhered to each other and to form cell aggregates and are settled on a culture surface. The culture solution containing cells which are on culture is not in the homogenous state, and hence it is necessary to mix the culture solution into the homogenous state at the time of sampling or measuring the turbidity. Since these operations cause the culture environment to change, the culture system cannot be evaluated, and hence it is difficult to measure the number of viable cells while continuing the culture. Since the number of cells sampled from a patient is scarce, it is required to avoid loss of the cells by measurement.

In the case of the manual cell culture, daily operation is performed on the basis of the culture evaluation depending on the experience of culture engineers, or the culture operation is performed homogenously for all the cells on the basis of a predetermined manual. Therefore, some of sampled cells may be insufficiently cultured in terms of cell proliferation or the like. In order to maximally educe the proliferation potential of cells which varies among each patient, an objective and adequate evaluation of the culture is necessary.

Therefore, Patent Document 1 discloses a method of evaluating cell proliferation potential in which the proliferation potential of the entire cell population can be figured by non-assaulting and nondestructive morphological observation and measurement of the respective adhered dependent cells.

Patent Document 2 discloses an apparatus for selecting the adhered cells by processing projected images from a CCD camera to know time required for the cells suspending in the culture medium in a culture vessel until it is adhered to a bottom surface of the culture vessel.

[Patent Document 1] JP-A-2002-218995
[Patent Document 2] JP-A-2003-21628

DISCLOSURE OF THE INVENTION

Problems to be Solved by the Invention

For example, in a customized medical treatment on the basis of the culture of cells, it is required to estimate and evaluate lag time and minimum doubling time as a proliferation potential of cells efficiently within a short time and to determine whether or not the cell population is stimulated for proliferation objectively and adequately when culturing cells sampled from a patient.

When the lag time (time of inductive phase) can be estimated and evaluated, the timing of initiation of proliferation of the inoculated cells can be estimated, so that the cells whose proliferation potential is remarkably lowered may be determined, and hence whether or not the culture is to be continued may be determined.

When the minimum doubling time can be estimated and evaluated, the proliferation potential of the cells in question can be estimated, so that the timing to add the culture medium according to the proliferation of the cells or the timing to change the culture vessel can be estimated. Therefore, the scheduling of the culture is enabled.

In addition, when whether or not the inoculated cell, population is stimulated for proliferation is determined objectively and adequately, objective and adequate determination for transferring the cell culture to a next stage (for example, for transferring the cells from the culture vessel for stimulation for proliferation to a vessel for proliferation) is achieved.

However, with the method of evaluating the proliferation potential of cells in the related art, although the proliferation potential of the entire cell population on culture may be figured, estimation of the timing of initiation of proliferation of the inoculated cell, estimation and evaluation of the minimum doubling time, and objective and adequate determination of whether or not the cell population is stimulated for proliferation are not achieved.

In order to solve the above-described problems, it is an object of the present invention to provide a cell culture evaluation system, a cell culture evaluation method, and a cell culture evaluation program which are capable of estimation and evaluation of lag time or minimum doubling time, and objective and adequate determination of whether or not the cell population is stimulated for proliferation by using an average cell projected area of a cell population on culture or the increasing rate of non-single-cells as an evaluation parameter in suspension culture.

Means for Solving the Problems

A cell culture evaluation system according to a first aspect of the present invention includes a culture device for static culture in a culture vessel and a measuring device for measuring cells to be cultured by the culture device, wherein the measuring device includes image acquiring means for acquiring images of a cell population in the culture vessel, average projected area calculating means for calculating an average projected area of cells from the images acquired by the image acquiring means at every culture time, lag time determining means for determining the lag time of the cultured cells from the average projected area of the cells calculated by the average projected area calculating means.

According to a second aspect of the present invention, the lag time determining means calculates the lag time of the cultured cells from a relational expression between the average projected area of the cells at the culture time and the lag time.

According to a third aspect of the present invention, the lag time determining means is employed as a parameter for evaluating a proliferation potential of the cell population.

A cell culture evaluation system according to a fourth aspect of the present invention includes means for calculating lag time from a proliferation profile of the number of cells in at least two samples, means for calculating the average projected areas of cells at the culture times of the respective samples, means for calculating correlation coefficients between the average projected areas and the lag times of the cells of the respective samples corresponding to the culture times, and means for calculating a relational expression between the average projected area corresponding to the culture time having the correlation coefficient equal to or higher than a reference value and the lag time.

The cell culture evaluation system according to a fifth aspect of the present invention includes a culture device for static culture in a culture vessel and a measuring device for measuring cells to be cultured by the culture device, wherein the measuring device includes image acquiring means for acquiring images of a cell population in the culture vessel, and cell morphology discriminating means for discriminating single-cells and non-single-cells which form cell aggregates from the images acquired by the image acquiring means.

A cell culture evaluation system according to a sixth aspect of the present invention includes a culture device for static culture in a culture vessel and a measuring device for measuring cells to be cultured by the culture device, wherein the measuring device includes image acquiring means for acquiring images of a cell population in the culture vessel, extracting means for extracting non-single-cells from the images acquired by the image acquiring means, means for calculating the ratio of the non-single-cells in the cell population from the extracting means, means for calculating the increasing rate of the non-single-cells from the means for calculating the ratio of the non-single-cells, and minimum doubling time determining means for determining the minimum doubling time of cultured cells from the increasing rate of the non-single-cells calculated by the means for calculating the increasing rate of the non-single-cells.

According to a seventh aspect of the present invention, the minimum doubling time determining means calculates the minimum doubling time of the cultured cells from a relational expression between the increasing rate of the non-single-cells in the cell population at the culture time and the minimum doubling time of the cell population.

According to an eighth aspect of the present invention, the increasing rate of the non-single-cells in the minimum doubling time determining means is employed as a parameter for evaluating the proliferation potential of the cell population.

A cell culture evaluation system according to a ninth aspect of the present invention includes means for calculating the increasing rate of the non-single-cells in at least two samples, means for calculating doubling times of the cells from the increasing rates of the non-single cells in the respective samples, means for employing the shortest time from among the calculated doubling times of the cells as a minimum doubling time, means for calculating the correlation coefficient between the increasing rate of the non-single-cells in a predetermined culture time and the minimum doubling time, and means for calculating a relational expression between the increasing rate of the non-single-cells having the correlation coefficient equal to or higher than a reference value and the minimum doubling time.

A cell culture evaluation system according to a tenth aspect of the present invention includes a culture device for static culture in a culture vessel and a measuring device for measuring cells to be cultured by the culture device, wherein the measuring device includes image acquiring means for acquiring images of a cell population to be cultured statically in the culture vessel, extracting means for extracting non-single-cells from the images acquired by the image acquiring means, means for calculating the ratio of the non-single-cells in a cell population from the extracting means, and means for determining whether or not the cell population is stimulated for proliferation from the ratio of the non-single-cells calculated by the means for calculating the ratio of the non-single-cells in the cell population.

A cell culture evaluation method according to an eleventh aspect of the present invention includes an image acquiring step for acquiring images of a cell population to be cultured statically in a culture vessel, an average projected area calculating step for calculating an average projected area of cells from images acquired in the image acquiring step at every culture time, and a lag time determining step for determining the lag time of the cultured cells from the average projected area of the cells calculated in the average projected area calculating step.

According to a twelfth aspect of the present invention, the lag time determining step calculates the lag time of the cultured cells from a relational expression between the average projected area of the cells at the culture time and the lag time.

According to a thirteenth aspect of the present invention, the average projected area of the cells in the lag time determining step is employed as a parameter for evaluating a proliferation potential of the cell population.

A cell culture evaluation method according to a fourteenth aspect of the present invention includes a step of calculating the lag time from a proliferation profile of the number of cells in at least two samples, a step of calculating the average projected areas of cells at the culture times of the respective samples, a step of calculating correlation coefficients between the average projected areas and the lag times of the cells of the respective samples corresponding to the culture times, and a step of calculating a relational expression between the average projected area of cells in the culture time having the correlation coefficient equal to or higher than a reference value and the lag time.

A cell culture evaluation method according to a fifteenth aspect of the present invention includes an image acquiring step for acquiring images of a cell population to be cultured statically in a culture vessel, and a cell morphology discriminating step for discriminating single-cells and non-single-cells which form cell aggregates from images acquired in the image acquiring step.

A cell culture evaluation method according to a sixteenth aspect of the present invention includes an image acquiring step for acquiring images of a cell population to be cultured statically in a culture vessel, an extracting step for extracting non-single-cells from images acquired in the image acquiring step, a step of calculating the ratio of the non-single-cells in the cell population on the basis of the result of the extracting step, a step of calculating the increasing rate of the non-single-cells in the step of calculating the ratio of the non-single-cells, and a minimum doubling time determining step for determining the minimum doubling time of cultured cells from the increasing rate of the non-single-cells calculated in the step of calculating the increasing rate of the non-single-cells.

According to a seventeenth aspect of the present invention, the minimum doubling time determining step includes calculating the minimum doubling time of the cultured cells from a relational expression between the increasing rate of the non-single-cells at the culture time and the minimum doubling time of the cell population.

According to an eighteenth aspect of the present invention, the increasing rate of the non-single-cells in the minimum doubling time determining step is employed as a parameter for evaluating the proliferation potential of the cell population.

A cell culture evaluation method according to a nineteenth aspect of the present invention includes a step of calculating the increasing rate of the non-single-cells in at least two samples, a step of calculating doubling times of the cells from the increasing rates of the non-single-cells in the respective samples, a step of employing the shortest time from among the calculated doubling times of the cells as a minimum doubling time, a step of calculating the correlation coefficient between the increasing rate of the non-single-cells in a predetermined culture time and the minimum doubling time, and a step of calculating a relational expression between the increasing rate of the non-single-cells having the correlation coefficient equal to or higher than a reference value and the minimum doubling time.

A cell culture evaluation method according to a twentieth aspect of the present invention includes an image acquiring step for acquiring images of a cell population to be cultured statically in a culture vessel, an extracting step for extracting non-single-cells from images acquired in the image acquiring step, a step of calculating the ratio of the non-single-cells in the cell population in the extracting step, and a step of determining whether or not the cell population is stimulated for proliferation from the ratio of the non-single-cells calculated in the step of calculating the ratio of the non-single-cells in the cell population.

A cell culture evaluation program according to a twenty-first aspect of the present invention is a cell culture evaluation program stored in a computer of a measuring device for measuring cells to be cultured in a culture device, the program causing the computer to execute an image acquiring procedure for acquiring images of a cell population to be cultured statically in a culture vessel, an average projected area calculating procedure for calculating an average projected area of cells from the images acquired in the image acquiring procedure at every culture time, and a lag time determining procedure for determining the lag time of the cultured cells from the average projected area of the cells calculated in the average projected area calculating procedure.

A cell culture evaluation program according to a twenty-second aspect of the present invention is a cell culture evaluation program stored in a computer of a measuring device for measuring cells to be cultured in a culture device, the program causing the computer to execute an image acquiring procedure for acquiring images of a cell population to be cultured statically in a culture vessel, a cell morphology discriminating procedure for discriminating single-cells and non-single-cells which form cell aggregates on the basis of the images acquired in the image acquiring procedure, an extracting procedure for extracting the non-single-cells on the basis of the result of the cell morphology discriminating procedure, a procedure for calculating the ratio of the non-single-cells in the cell population on the basis of the result of the extracting procedure, a procedure for calculating the increasing rate of the non-single-cells on the basis of the result of the procedure for calculating the ratio of the non-single-cells, and a minimum doubling time determining procedure for determining the minimum doubling time on the basis of the result of the procedure for calculating the increasing rate of the non-single-cells.

A cell culture evaluation program according to a twenty-third aspect of the present invention is a cell culture evaluation program stored in a computer of a measuring device for measuring cells to be cultured in a culture device, the program causing the computer to execute an image acquiring procedure for acquiring images of a cell population to be cultured statically in a culture vessel, a cell morphology discriminating procedure for discriminating single-cells and non-single-cells which form cell aggregates from the images acquired in the image acquiring procedure, an extracting procedure for extracting the non-single-cells on the basis of the result of the cell morphology discriminating procedure, a procedure for calculating the ratio of the non-single-cells in the cell population on the basis of the result of the extracting procedure, and a procedure for determining whether or not the cell population is stimulated for proliferation from the ratio of the non-single-cells calculated in the procedure for calculating the ratio of the non-single-cells in the cell population.

Advantages

With the cell culture evaluation system, the cell culture evaluation method, and the cell culture evaluation program according to the present invention, by estimating and evaluating the lag time, the time point when the proliferation of the inoculated cells initiates can be estimated, so that the cells whose proliferation potential is remarkably lowered can be determined, and hence whether or not the culture to be continued can be determined.

With the cell culture evaluation system, the cell culture evaluation method, and the cell culture evaluation program according to the present invention, by estimating and evaluating the minimum doubling time, the proliferation potential of the cells in question can be estimated, so that the timing to add the culture medium according to the proliferation of the cells or the timing to change the culture vessel or the like can be estimated. Therefore, the scheduling of the culture is enabled.

With the cell culture evaluation system, the cell culture evaluation method, and the cell culture evaluation program according to the present invention, whether or not the inoculated cell population is stimulated for proliferation can be determined by calculating the ratio of the non-single-cells, so that objective and adequate determination for transferring the cell culture to a next stage (for example, for transferring the cells from the culture vessel for stimulation for proliferation to a vessel for proliferation) is achieved.

When the lag time or the minimum doubling time of the estimated and evaluated culture system is too long, or when it is determined that the cell population is not stimulated for proliferation form the ratio of the non-single-cells, the processing corresponding thereto can be performed quickly.

With the cell culture evaluation system, the cell culture evaluation method, and the cell culture evaluation program according to the present invention, when culturing cells sampled from the patient in the customized medical treatment, the lag time and the minimum doubling time as the proliferation potential can be estimated and evaluated efficiently within a short time without destructing and invading the cells. Also, objective and adequate determination whether or not the cell population is stimulated for proliferation is achieved from the ratio of the non-single-cells.

Figure 1:
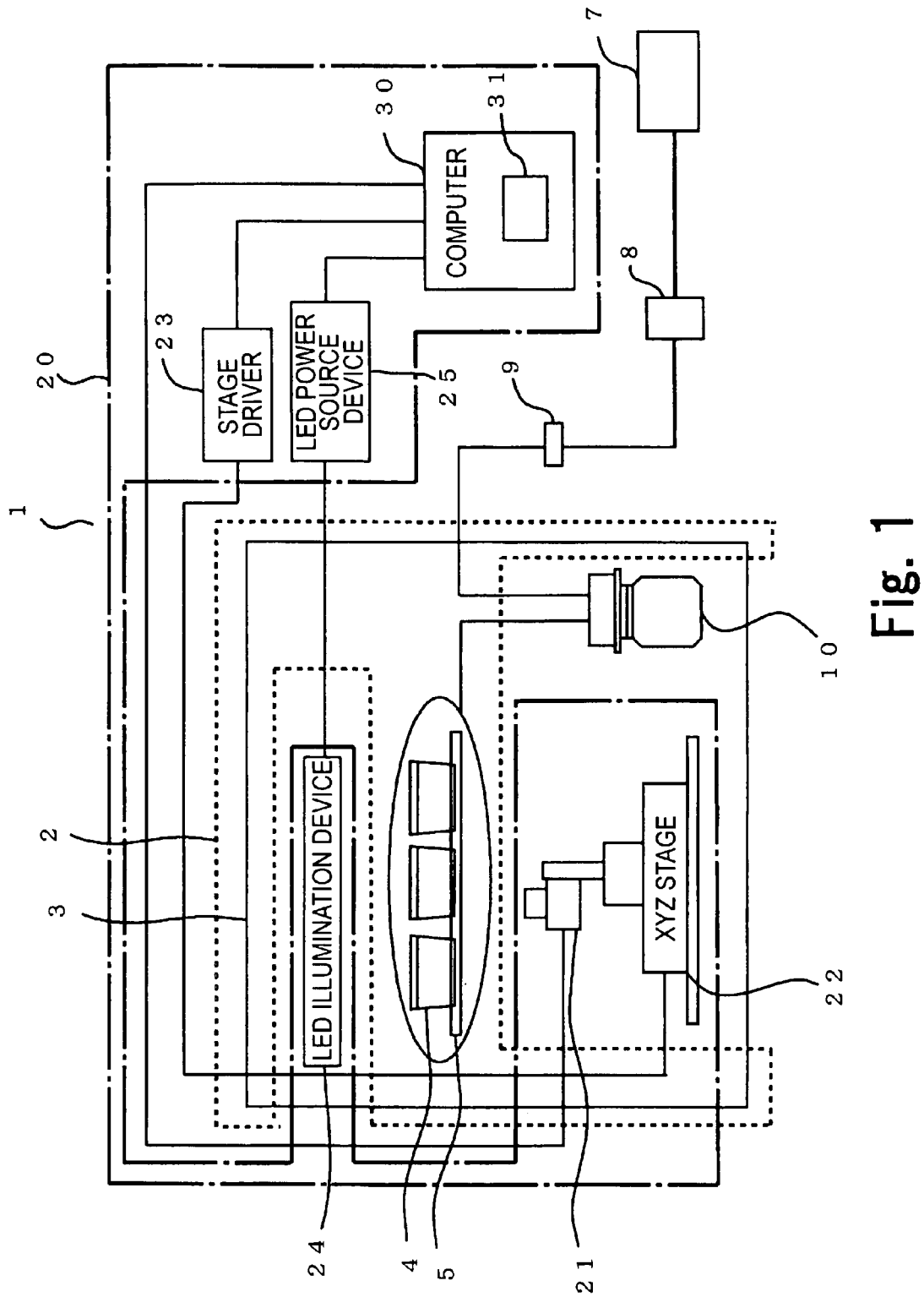
FIG. 1 is a block diagram showing a configuration of a cell culture evaluation system.

REFERENCE NUMERALS 1 cell culture evaluation system
2 culture device
3 incubator
4 culture vessel
5 culture vessel stage
7 gas cylinder
8 flow meter
9 filter
10 humidifying bottle
20 measuring device
21 CCD camera
22 XYZ stage
23 stage driver
24 LED illumination device
25 LED power source device
30 computer
31 video memory circuit

BEST MODE FOR CARRYING OUT THE INVENTION

Referring now to the drawings, a cell culture evaluation system, a cell culture evaluation method, and a cell culture evaluation program according to the present invention will be described. The cell culture evaluation system, the cell culture evaluation method, and the cell culture evaluation program according to the present invention are adapted so as to be capable of estimating and evaluating the lag time or the minimum doubling time as the proliferation potential by using an average cell projected area of a cell population on culture or the increasing rate of non-single-cells as an evaluation parameter when culturing suspension cells, and are also adapted so as to be capable of determining whether or not the cell population is stimulated for proliferation from the ratio of the non-single-cells.

Referring now to FIG. 1, a configuration of the cell culture evaluation system will be described. FIG. 1 is a block diagram showing a configuration of the cell culture evaluation system. As shown in FIG. 1, a cell culture evaluation system 1 includes a culture device 2 for culturing cells, and a measuring device 20 for measuring the cells to be cultured in the culture device 2. A portion surrounded by a dot line in FIG. 1 is the culture device 2 and a portion surrounded by a double-dashed chain line in FIG. 1 is the measuring device 20. The culture device 2 of the cell culture evaluation system 1 includes an incubator 3 for culturing the cells by keeping a certain temperature, a culture vessel (a flask or the like) 4 for culturing the cells, and a culture vessel stage 5 for mounting the culture vessel 4. The culture device 2 also includes a flow meter 8 for controlling the flow rate of mixed gas to be supplied from a gas cylinder 7 or the like to the culture vessel 4, a filter 9 positioned between the flow meter 8 and a humidifying bottle 10, and the humidifying bottle 10 for humidifying the mixed gas. The mixed gas to be supplied to the culture vessel 4 may be selected as needed depending on the type of the cells to be cultured. The mixed gas to be supplied from the gas cylinder 7 or the like is adapted to flow from the flow meter 8 through the filter 9, and then pass through the humidifying bottle 10 and be supplied to the culture vessel 4.

The measuring device 20 of the cell culture evaluation system 1 includes a XYZ stage 22 stored in the interior of the incubator 3, a CCD camera 21 as image acquiring means which is mounted to the XYZ stage 22 and is capable of moving in the three-dimensional direction, and an LED illumination device 24 mounted to the XYZ stage 22 and is capable of moving in the two-dimensional direction together with the CCD camera 21.

The XYZ stage 22 is provided with motors for driving an X-axis, a Y-axis, and a Z-axis of the stage, and the respective motors are controlled by a stage driver 23 to move to predetermined positions for performing positioning.

The CCD camera 21 mounted to the XYZ stage 22 is adapted to pick up images of a bottom portion of the culture vessel 4 placed on the culture vessel stage 5. The CCD camera 21 is capable of moving in the vertical direction by the XYZ stage 22, so that focusing of the CCD camera 21 is achieved.

The LED illumination device 24 is set to be positioned right above the CCD camera 21 through the culture vessel 4, so that control of illumination and extinction and control of illumination intensity may be performed by an LED power source device 25.

It is also possible to use other illumination devices such as an optical fiber illumination device in which light from a light source is guided through a fiber instead of the LED illumination device 24 positioned right above the culture vessel 4. The CCD camera 21 as the image acquiring means may be replaced by other image sensors such as a MOS-type camera.

As shown in FIG. 1, the measuring device 20 of the cell culture evaluation system 1 includes a computer 30 for processing image data from the CCD camera 21, control of the stage driver 23 and the LED power source device 25, and estimation of the lag time or the minimum doubling time of the cells on culture.

The computer 30 includes a CPU for calculation and control, a storage (memory) for storing a processing program and data, an input/output circuit for connecting keyboard and a mouse as input devices for entering data, commands and so on, and a monitor and the like as an output device, and a video memory circuit 31 for storing video data from the CCD camera 21. The video data from the CCD camera 21 is stored in a memory in the video memory circuit 31. The video data stored in the memory is readable by the CPU. The computer 30 is adapted to be capable of controlling the stage driver 23 for controlling the motor for driving the X-axis, the Y-axis and the Z-axis, and the LED power source device 25 for controlling the LED illumination device 24.

The computer 30 stores a control program for controlling the stage driver 23 and the LED power source device 25 to store the image data in the CCD camera 21 in the memory of the video memory circuit 31, an image processing program for analyzing and processing the image data stored in the memory of the video memory circuit 31, an arithmetic processing program for performing arithmetic processing such as calculation of the correlation coefficient or calculation of a relational expression by a least square method, an estimation processing program for performing estimation processing of the lag time or the minimum doubling time of the cells on culture, and so on. The computer 30 is adapted to execute these programs to evaluate the cell culture.

Subsequently, a cell culture evaluation method for the suspension cells using the cell culture evaluation system 1 configured as described above. The known suspension cells includes peripheral blood mononuclear cells, LAK cells, neural stem cells, ES cells, and the cell culture evaluation system, the cell culture evaluation method, and the cell culture evaluation program according to the present invention is applied to these cells. These suspension cells are referred simply as cells, hereinafter.

In order to evaluate the proliferation potential of the cells in the culture vessel 4, the lag time and the minimum doubling time are used. Here, the lag time means a time span of lag phase required for stating the proliferation from a moment when the cells are inoculated. The minimum doubling time means a time span required until the number of cells at a certain time point is doubled from that time point. The stimulation for proliferation means that an antibody stimulates the cells to promote the proliferation after the initiation of the culture.

When the lag time can be estimated and evaluated, the time point when the proliferation of the inoculated cells is initiated can be estimated, so that the cells whose proliferation potential is remarkably lowered can be determined, and hence whether or not the culture is to be continued can be determined.

When the minimum doubling time can be estimated and evaluated, the proliferation potential of the cells in question can be estimated, so that the timing to add the culture medium according to the proliferation of the cells or the timing to change the culture vessel or the like can be estimated. Therefore, the scheduling of the culture is enabled.

When whether or not the cell population is stimulated for proliferation can be determined automatically by calculating the ratio of the non-single cells, objective and adequate determination for transferring the cell culture to a next stage (for example, for transferring the cells from the culture vessel for stimulation for proliferation to a vessel for proliferation) can be performed is achieved.

Referring firstly to a flowchart shown in FIG. 2, a step of calculating the lag time from an average projected area of the cells on culture will be described as a first embodiment.

Figure 2:
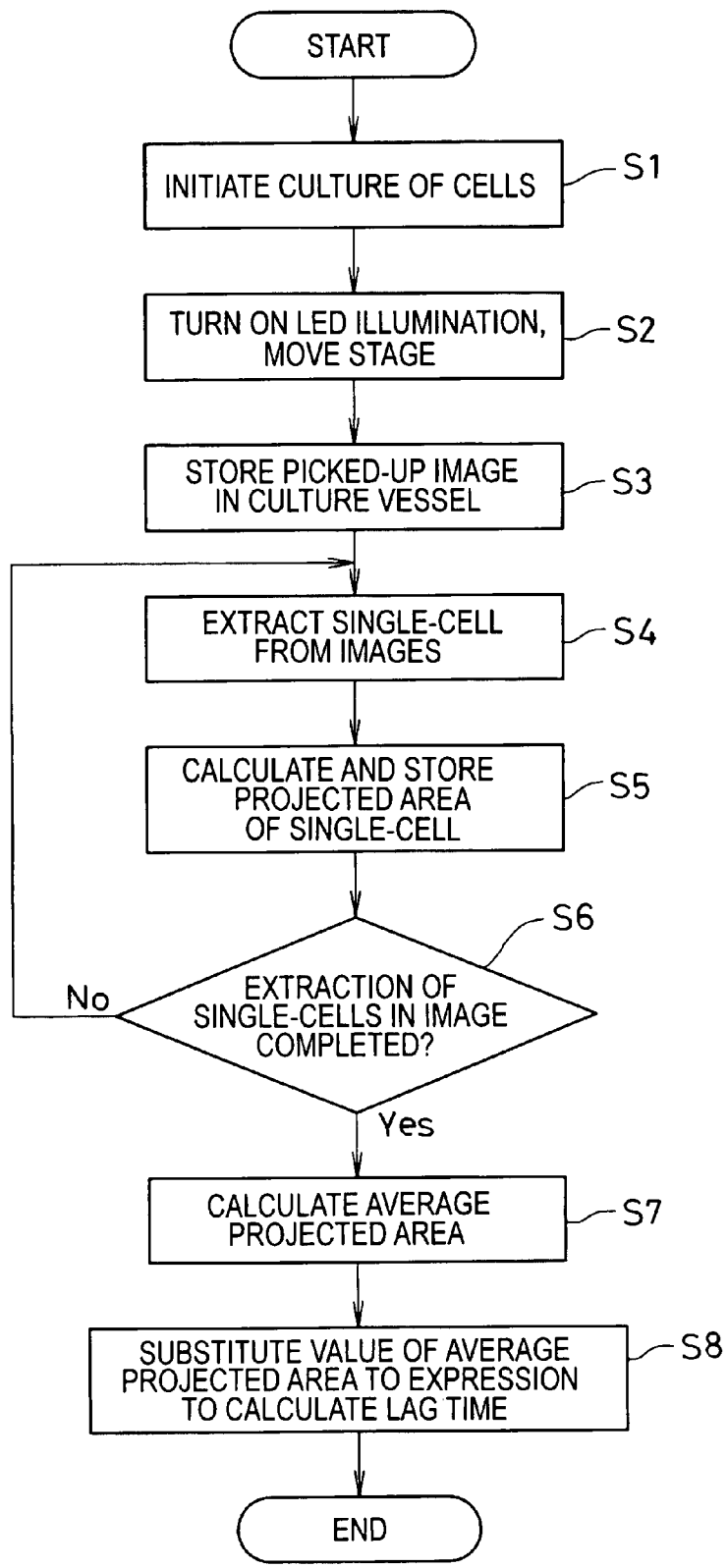
FIG. 2 is a flowchart showing a step of calculating the lag time for the average projected area of cells.

As shown in FIG. 2, the cells suspended in the culture medium are inoculated to the culture vessel 4 (shown in FIG. 1) of which culture surface is immobilized with an antibody for stimulating the cells for proliferation and the culture is initiated (Step S1). The antibody to be immobilized is selected adequately from the cells to be inoculated. For example, when culturing the LAK cells, an anti CD3 antibody is immobilized.

As a method of immobilizing the antibody, for example, the anti CD3 antibody is dissolved in physiologic saline or the like to obtain anti CD3 antibody solution, then the obtained solution is immersed on the culture surface of the culture vessel, and is kept stand still at a room temperature. A preferable time span to keep it stand still is on the order of one hour. Then, the culture surface is washed with the physiologic saline or the like, which is used for the culture. The number of cells to be inoculated is, for example, in the case of culturing the LAK cells, preferably at least $2.2 \times 10^4/cm^2$ per culture surface area used. It is because that the proliferation may be lowered when being inoculated with a value less than the value shown above.

The computer 30 of the measuring device 20 shown in FIG. 1 outputs a control signal to the LED power source device 25 after having elapsed 24 hours from the initiation of the culture to illuminate the LED illumination device 24 positioned right above the CCD camera 21 via the culture vessel 4, so that the images of cells and non-single-cells which form a cell aggregate may be analyzed easily by illuminating from above the culture vessel 4. The computer 30 also controls the stage driver 23 to move the XYZ stage 22 so that the distal end portion of a lens of the CCD camera 21 is located, for example, near the center of the bottom surface of the culture vessel 4 (Step S2).

Subsequently, the images are picked up by the CCD camera 21 from the bottom surface of the culture vessel 4, and the image data from the CCD camera 21 is stored in the video memory circuit 31 in the computer 30 (Step S3). The computer 30 executes the image processing program to read out the image data stored in the video memory circuit 31 and binarize the same. The single-cells are extracted from the binarized image data (Step S4). The projected areas of the extracted single-cells are measured and the measured values are stored in the memory (Step S5). Whether or not the extraction of all the single-cells in the image is completed is checked (Step S6), and the average projected areas of the single-cells are calculated after having finished the measurement for all the single-cells (Step S7). A step of calculating the average projected areas for calculating the average projected areas of the single-cells are executed by the computer 30 as average projected area calculating means.

Figure 3:
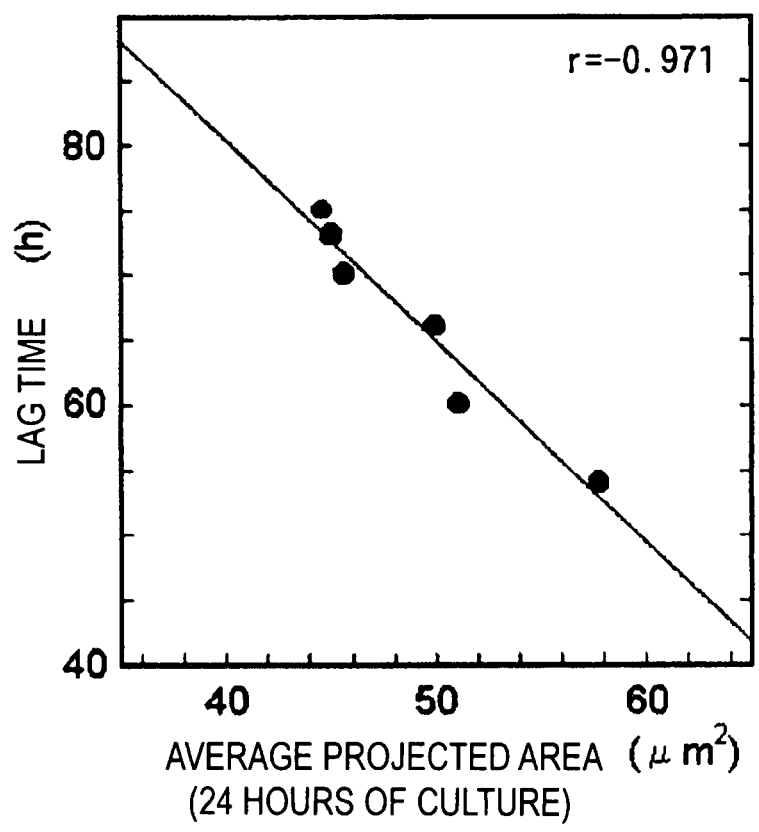
FIG. 3 is a graph showing a relation between the average projected area and the lag time.

Subsequently, the computer reads out a relational expression of the average projected areas of the single-cells and the lag times which are integrated in advance (linear equation shown in (1) described below) from the memory, substitutes the calculated value of the average projected areas of the cells in the relational expression, and calculates the lag times (Step S8). A lag time determination step of calculating the lag times is executed by the computer 30 as lag time determination means. FIG. 3 is a graph showing a relation between the average projected areas and the lag times. The relational expressions between the average projected areas of the single-cells and the lag times are derived from the straight line shown in FIG. 3. As described above, the lag times are calculated from the average projected areas of the cells by measuring the average projected areas of the cells using the cell images on culture picked up after having elapsed 24 hours from the initiation of the culture, so that the lag times as the proliferation potential of the cells in the corresponding cultures can be evaluated.

Figure 4:
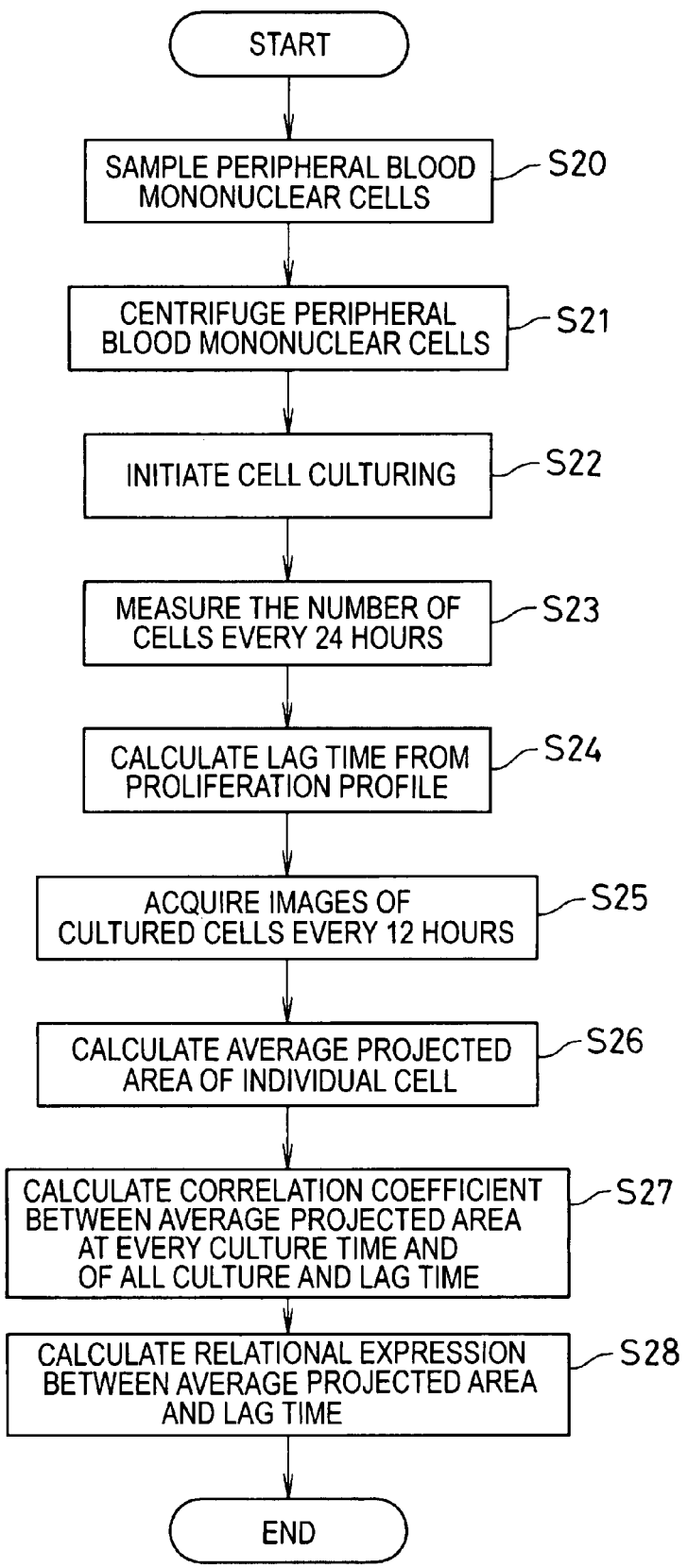
FIG. 4 is a flowchart showing a procedure for calculating a relational expression for estimating the lag times.
Figure 5:
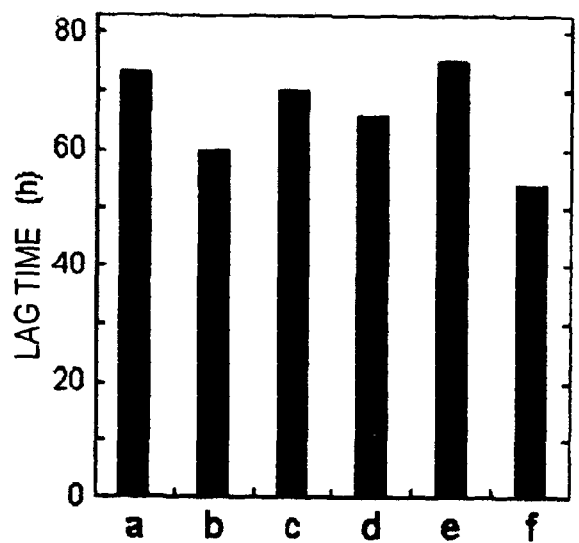
FIG. 5 is a drawing showing the lag times of LAK cells in six cultures (a to f).
Figure 6:
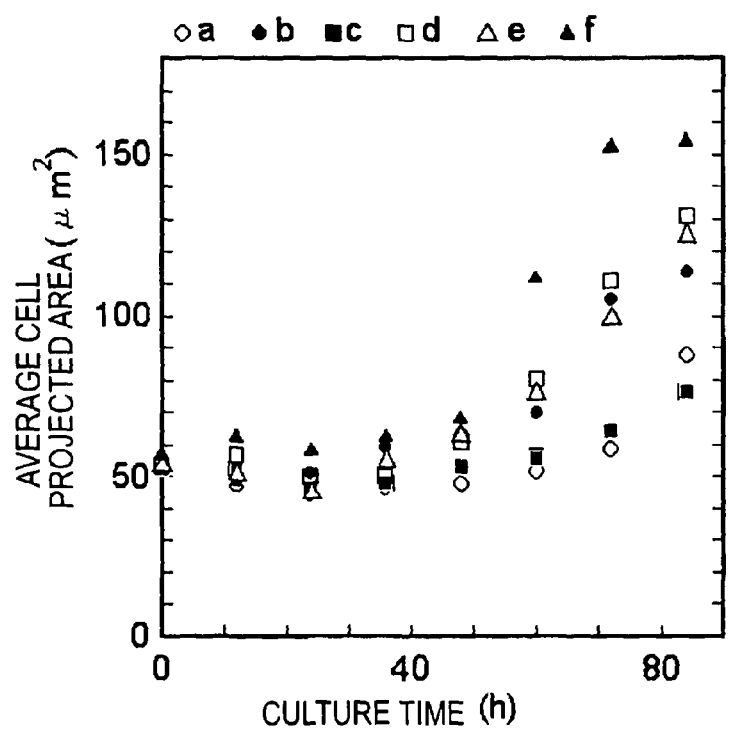
FIG. 6 is a drawing showing the change of the average projected area of cells at the culture times in the six cultures (a to f)

Referring now to FIG. 3 to FIG. 6, the calculation of the relational expression for estimating the lag times from the average projected areas of the single-cells will be described. FIG. 4 is a flowchart showing a procedure for calculating a relational expression for estimating the lag times, FIG. 5 is a drawing showing the lag times of the LAK cells in the six cultures (a to f), and FIG. 6 is a drawing showing the change of the average projected areas of the cells at the culture time in the six cultures (a to f).

Referring now to the flowchart in FIG. 4, a procedure for calculating the relational expression for estimating the lag times will be described. As shown in FIG. 4, the peripheral blood mononuclear cells are sampled first (Step S20). Sampling of the peripheral blood mononuclear cells is achieved by drawing peripheral blood from different donors by 7.5 ml using a vacuum blood collecting tube. The number of samples is six, and reference signs from a to f are assigned thereto respectively. The sampled peripheral blood is separated to obtain human peripheral blood mononuclear cells by means of centrifugation (1710×g, 20 min.) (Step S21).

Subsequently, a culture medium including self blood plasma 8% and the peripheral blood mononuclear cells are inoculated to a 6-well culture vessel of which culture surface is immobilized with an anti CD3 antibody so as to be $2.2 \times 10^4/cm^2$, and is cultured in the incubator 3 maintained at a temperature of 37° C. and 5% $CO_2$ air (Step S22).

Sampling is performed every 24 hours during seven days culture period, and the picked-up images of the cultured cells or a blood cell counting chamber is used for obtaining the number of cells (Step S23). From the result, the proliferation profiles of the cells are prepared, and inclination of the graphs in the lag phase and a logarithmic growth phase are calculated by the least square method, and an intersection of the two graphs is calculated as the lag times (Step S24, a step of calculating the lag time). The step of calculating the lag time is executed by the computer 30 as lag time calculating means.

FIG. 5 is a drawing showing the lag times of the LAK cells in the six cultures (a to f). As shown in FIG. 5, the lag times as the length of the lag period from the inoculation of the cells to the initiation of the culture is distributed over a wide range from 54 hours to 75 hours in the six cultures (a to f).

The change of behavior of the individual cell in the respective cultures is observed during the culture period, and the change in behavior of the cells was found to be enlarged significantly in all the cultures (a to f). The images of the cultured cells are picked up at every 12 hours for 84 hours of culture by the cell culture evaluation system 1 shown in FIG. 1 (Step S25), and the average projected area is calculated for the individual cell (Step S26, a step of calculating the average, projected area). The step of calculating the average projected area is executed by the computer 30 as means for calculating the average projected area.

FIG. 6 is a drawing showing the change of the average projected areas of the cells at the culture time in the six cultures (a to f). As shown in FIG. 6, the average projected areas immediately after the inoculation stay at about 50 μm² in every cultures (a to f), and then from the 75 hours of culture on, the cells were initiated to be enlarged, and the average projected areas were tend to increase. FIG. 6 also shows that the tendency of increase in the cell projected area varies among cultures, and relates to the proliferation potential in each culture.

Then, the correlation coefficients between the average projected areas in the respective cultures (a to f) for every culture time shown in FIG. 6 and the lag times in the cultures (a to f) in FIG. 3 are calculated (Step S27, a step of calculating the correlation coefficient. The step of calculating the correlation coefficient is executed by the computer 30 as means for calculating the correlation coefficient.

As shown in FIG. 3, when the relation between the average cell projected areas and the lag times in the respective cultures (a to f) at the 24 hours of culture is calculated, a correlation demonstrating a coefficient as high as −0.971 was obtained. In other words, the lag time in a certain culture can be estimated and evaluated by picking up the cell images at the 24 hours of culture time and using the average projected area as the evaluation parameter. The relational expression is calculated by the least square method from the average projected area and the lag time whose correlation coefficient is closest to −1 (Step S28, a step of calculating a relational expression). The calculated correlation coefficient may be compared with a reference value (for example, the correlation coefficient in the range from −1 to −0.9) which is set in advance to select the one which is equal to or larger than the reference value (which satisfies the reference value). The process of calculating a relational expression is performed by the computer 30 as the means for calculating the relational expression. The relational expression is expressed by a linear equation shown in (1) relating to the average projected area $A_C$ and the lag time $t_L$.

$$t_L = a \times A_C + b \qquad (1)$$

where a and b are coefficients calculated by the least square method. The lag time $t_L$ is calculated by substituting the average projected area $A_C$ as the evaluation parameter into the linear equation of (1).

In this manner, the relational expression for estimating the lag time from the average projected area is calculated, and the calculated relational expression is stored in the computer 30, which is used in the step of estimating the lag time.

Figure 7:
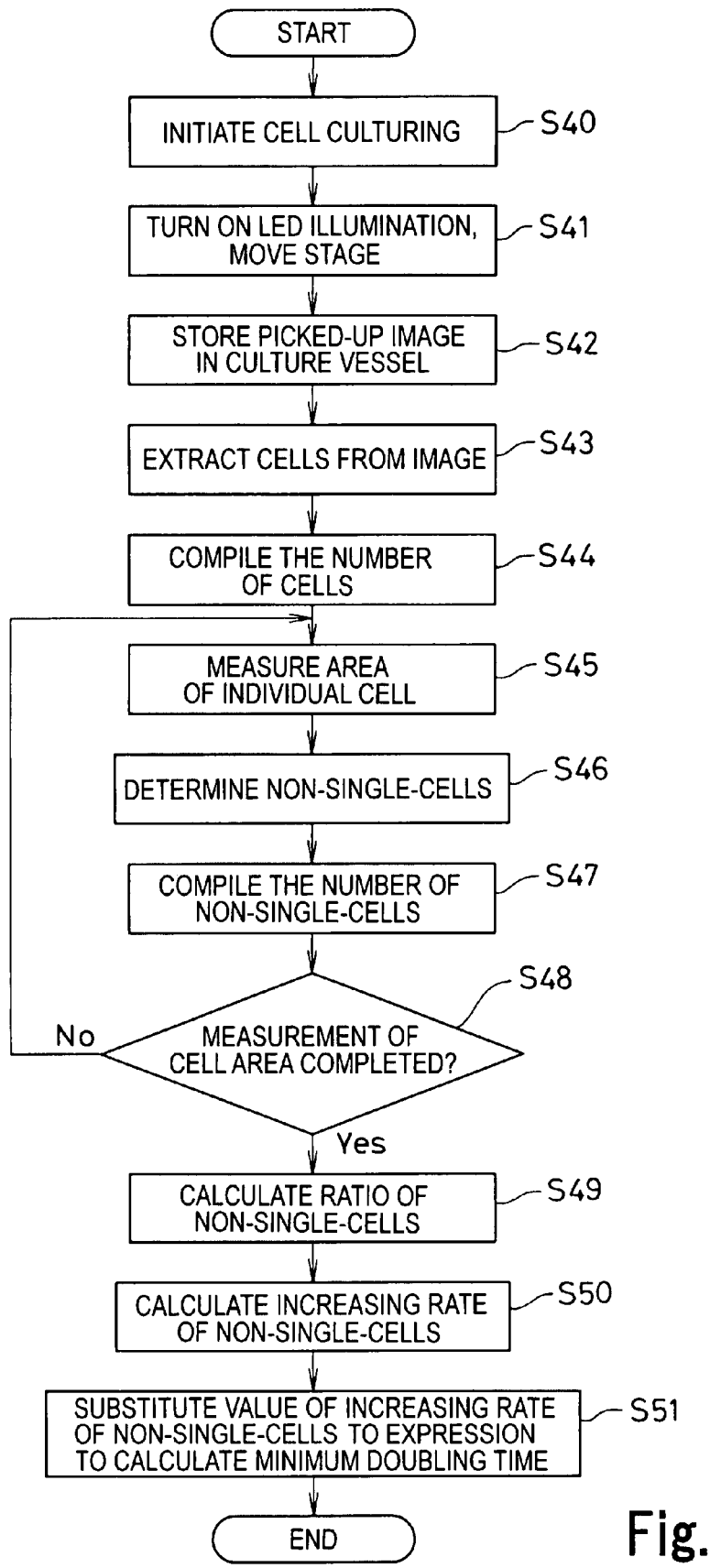
FIG. 7 is a flowchart showing a step of calculating a minimum doubling time from the increasing rate of non-single-cells among cells.

Referring now to a flowchart in FIG. 7, a step of calculating the minimum doubling time from the increasing rate of the non-single-cells which form cell aggregates will be described as a second embodiment.

The cells suspended in the culture medium are inoculated to the culture vessel 4 of which culture surface is immobilized with an antibody for simulating the cells for proliferation to initiate the culture (Step S40). The computer 30 outputs control signals to the LED power source device 25 after having elapsed 24 hours, 48 hours, and 72 hours from the initiation of the culture to illuminate the LED illumination device 24 positioned right above the CCD camera 21 via the culture vessel 4, so that the images of cells and non-single-cells which form a cell aggregate may be analyzed easily by illuminating from above the culture vessel 4. The computer 30 also controls the stage driver 23 to move the XYZ stage 22 so that the distal end portion of the lens of the CCD camera 21 is located, for example, near the center of the bottom surface of the culture vessel 4 (Step S41). Subsequently, the images are picked up by the CCD camera 21 from the bottom surface of the culture vessel 4 after having elapsed 24 hours, 48 hours, and 72 hours from the initiation of the culture, and the image data is stored in the video memory circuit 31 in the computer 30 (Step S42).

Subsequently, the computer reads out the image data stored in the video memory circuit 31 and binarizes the same. The cells are extracted from the binarized image data (Step S43), and the number of extracted cells is compiled (Step S44). The projected areas of the extracted cells are measured (Step S45).

Subsequently, the extracted cells are discriminated between the single-cells and the non-single-cells which form the cell aggregate. Discrimination between the single-cells and the non-single-cells is done by determining those having the projected area equal to or larger than 100 $\mu m^2$ to be the non-single-cells (Step S46). The reference that the cells having the projected area equal to or larger than 100 $\mu m^2$ are determined to be non-single-cells is based on the fact that the projected area of the single-cell at the beginning of culture is smaller than 100 $\mu m^2$ at the maximum, and those having the projected area equal to or larger than 100 $\mu m^2$ means that two or more cells are in contact with each other, and hence form a non-single-cell. A step of discriminating the cell morphology for discriminating the single-cells and the non-single-cells is executed by the computer 30 as cell morphology discriminating means.

Subsequently, the discriminated non-single-cells are extracted and the number of the extracted non-single-cells is compiled (Step S47). Whether or not the measurement of the projected areas of all the cells is completed is checked (Step S48). After having completed the measurement of the projected areas of all the cells, the ratio of the non-single-cells with respect to the number of cells compiled in Step S44 is calculated (Step S49). The increasing rate of the non-single-cells is calculated from the change of the ratio of the non-single-cells calculated after 24 hours, 48 hours, and 72 hours from the initiation of the culture (Step S50). An extracting step of extracting the non-single-cells, a step of calculating the ratio of the non-single-cells, and a step of calculating the increasing rate of the non-single-cells are executed by the computer 30 as means for extracting the non-single-cells, means for calculating the ratio of the non-single-cells, and means for calculating the increasing rate of the non-single-cells.

Figure 8:
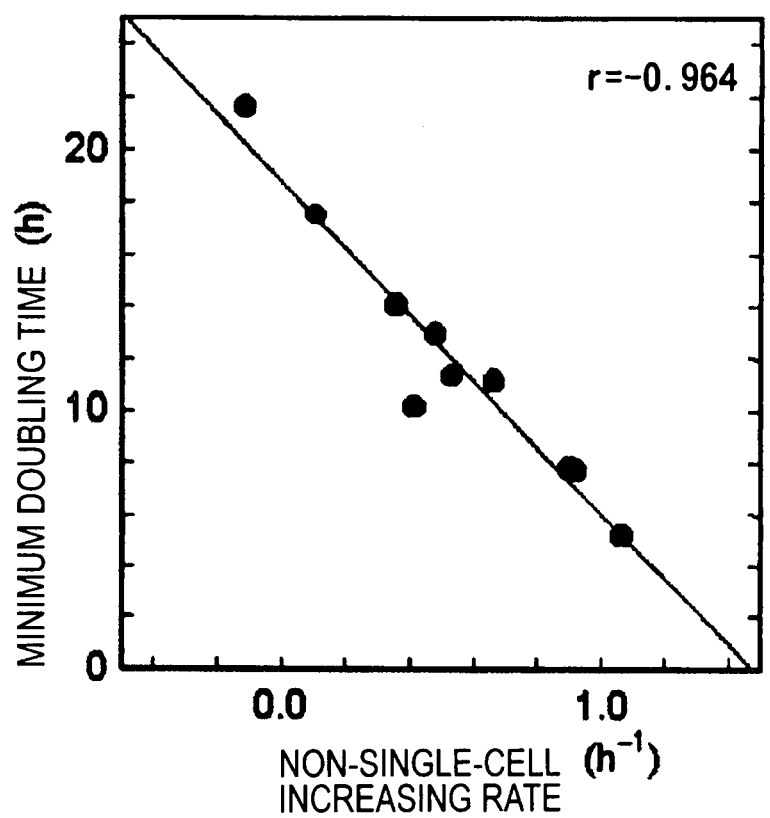
FIG. 8 is a graph showing a relation between the increasing rate of the non-single-cells and the minimum doubling time.

Then, the computer substitutes the calculated valve of the increasing rate of the non-single-cells into the relational expression between the calculated increasing rate of the non-single-cells and the minimum doubling time (a linear equation shown in (2) described later) and calculates the minimum doubling time (Step S51). A minimum doubling time determining step of calculating the minimum doubling time is executed by the computer 30 as minimum doubling time determining means. FIG. 8 is a graph showing a relation between the increasing rate of the non-single-cells and the minimum doubling time. The relational expression between the increasing rate of the non-single-cells and the minimum doubling time is derived from the straight line shown in FIG. 8.

In other words, the minimum doubling time as the proliferation potential in the culture from 24 hours to 72 hours of culture time can be evaluated by measuring the projected areas of the cells and the non-single-cells by the cell images picked up with time during the culture, calculating the ratio of the non-single-cells with time, and calculating the increasing rate of the non-single-cells in the corresponding culture.

Figure 9:
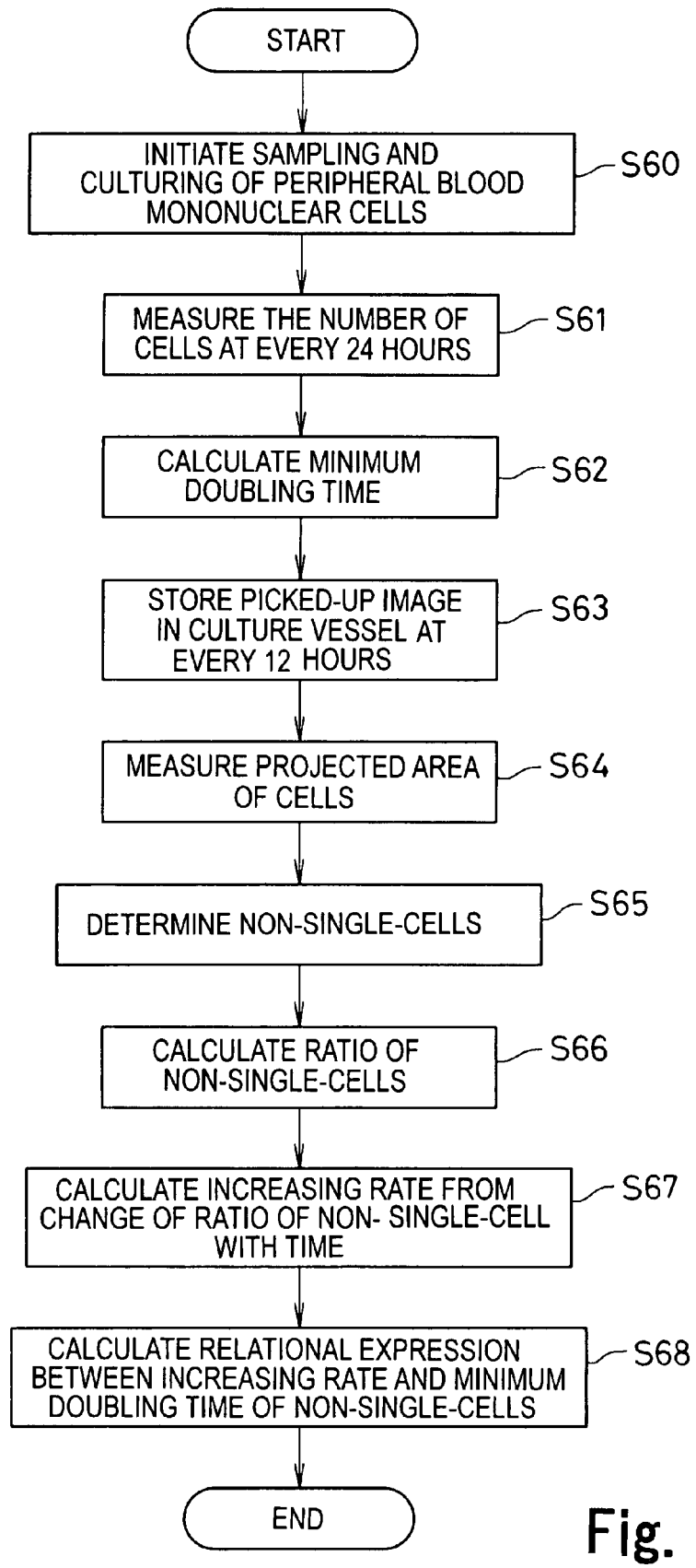
FIG. 9 is a flowchart showing a step of calculating a relational expression for estimating and evaluating the minimum doubling time using the increasing rate of the non-single-cells.
Figure 10:
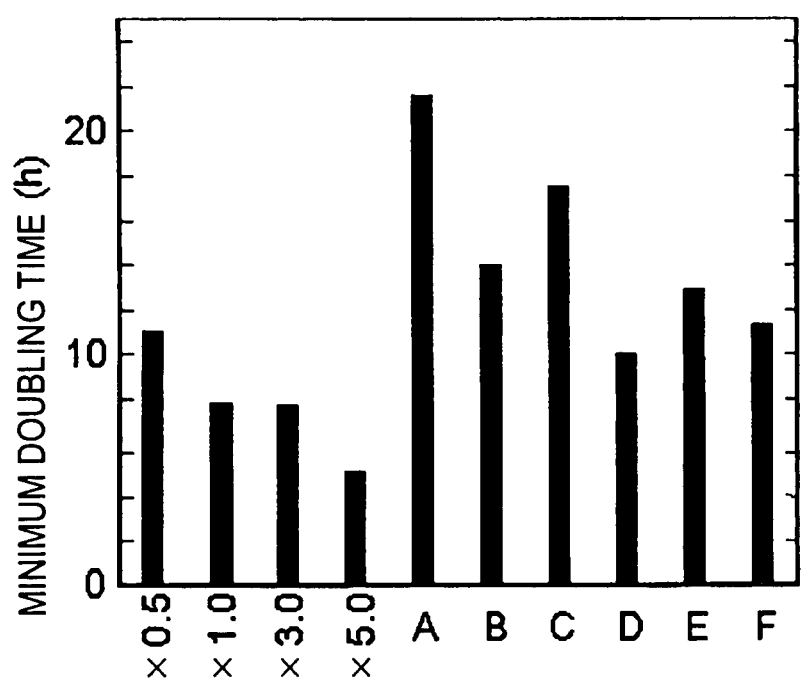
FIG. 10 is a drawing showing the minimum doubling time of the LAK cells in cultures depending on the difference in concentration of inoculated cells and in cultures (A to F) having different samples.
Figure 11:
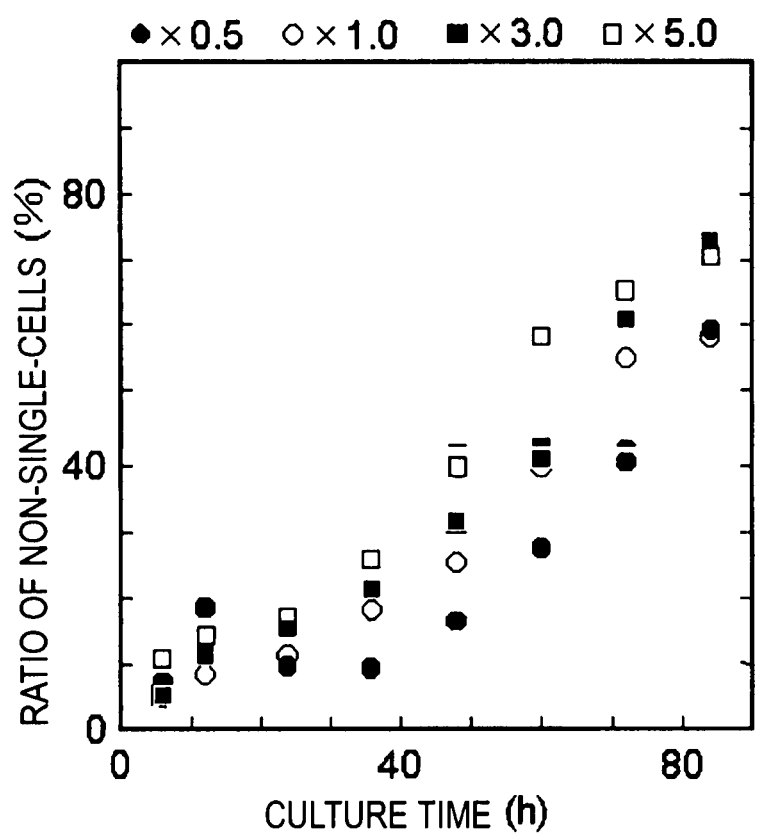
FIG. 11 is a drawing showing the change of the ratio of the non-single-cells at the culture time in the cultures (×0.5 to ×5.0) depending on the difference in concentration of inoculated cells.
Figure 12:
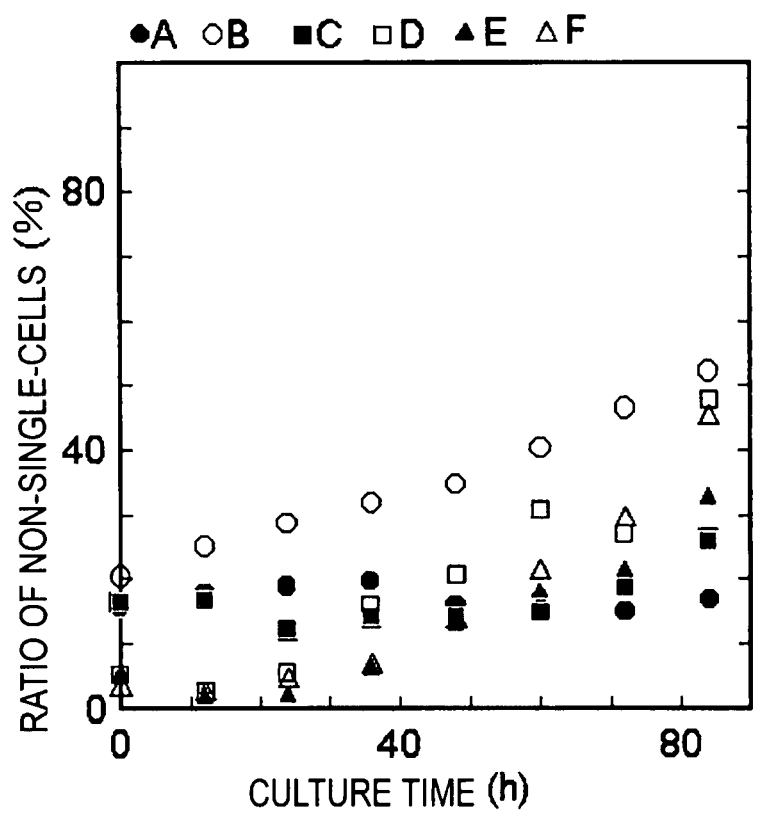
FIG. 12 is a drawing showing the change of the ratio of the non-single-cells at the culture time in the cultures (A to F) having different samples.

Referring now to FIG. 8 to FIG. 12, the calculation of the relational expression for estimating the minimum doubling time using the increasing rate of the non-single-cells will be described. FIG. 9 is a flowchart showing a step of calculating the relational expression for evaluating and estimating the minimum doubling time using the increasing rate of the non-single-cells, FIG. 10 is a drawing showing the minimum doubling time of the LAK cells in the cultures depending on the difference in concentration of the inoculated cells and cultures (A to F) having different samples, FIG. 11 is a drawing showing the change of ratio of the non-single-cells at the culture time in the cultures having different concentration of the inoculated cells (×0.5 to ×5.0), and FIG. 12 is a drawing showing the change of ratio of the non-single-cells at the culture time in the cultures (A to F) having different samples.

Referring now to a flowchart in FIG. 9, a procedure for calculating the relational expression for estimating the minimum doubling time will be described.

A culture medium including self blood plasma 8% and the peripheral blood mononuclear cells are inoculated to the culture vessel 4 of which culture surface is immobilized with an anti CD3 antibody so as to be $2.2 \times 10^4/cm^2$ and cells used here are cultured in the incubator 3 maintained at a temperature of 37° C. and 5% $CO_2$ air (Step S60).

The number of sampled samples is seven and one of these samples is used to prepare various concentrations of the inoculated cells (×0.5, ×1.0, ×3.0, and ×5.0), reference signs A to F are assigned to other six samples. Data of the concentration of the inoculated cells, ×0.5, ×3.0, and ×5.0 means to inoculate at densities of ½ times, three times, and five times the concentration of $2.2 \times 10^4/cm^2$ as ×1.0.

Sampling is performed every 24 hours during seven days culture period, and a blood cell counting chamber is used for obtaining the number of cells (Step S61). The increasing rate of the non-single-cells during 48 hours is obtained by the least square method every 24 hours (a step of calculating the increasing rate) to calculate the doubling time of the cells (a step of calculating the doubling time). The shortest time from among the doubling times taken at every 24 hours is employed as the minimum doubling time (Step S62, a step of employing the shortest time as the minimum doubling time). The step of calculating the increasing rate, the step of calculating the doubling time, and the step of employing the shortest time as the minimum doubling time are executed by the computer 30 as means for calculating the increasing rate, means for calculating the doubling time, and means for employing the shortest time as the minimum doubling time.

FIG. 10 is a drawing showing the cultures (×0.5, ×1.0, ×3.0, and ×5.0) depending on the difference in concentration of the inoculated cells and the minimum doubling times of the LAK cells in the cultures (A to F) having different samples.

As shown in FIG. 10, it was found that, the higher the concentration of the inoculated cells, the smaller the value of the minimum doubling time in the case of the cultures (×0.5 to ×5.0) depending on the difference in concentration of the inoculated cells. On the other hand, the minimum doubling time varies among the cultures (A to F) having different samples, so that it was found that the proliferation potential of the cells varies among each sample Subsequently, the cells are cultured through the same procedure as Step S60, and the images are picked up at every 12 hours until 84 hours of culture time has elapsed in the respective cultures (Step S63) and the projected areas are measured from the picked-up image (Step S64). It will be found that the inoculated cells are stimulated by the immobilized antibody on the culture surface, and the cells come into contact with each other frequently. Each cell moves on the culture surface as it rolls thereon, and when it meets another cell, these cells come into contact with each other to form the non-single-cell. Then, the non-single-cells positively join to form a larger non-single-cell.

Therefore, utilizing the fact that the projected surface area of the single-cell at the beginning of the culture is smaller than 100 μm² at the maximum, the cells having the projected areas equal to or larger than 100 μm² are determined as the non-single cells (Step S65). The cells having the projected areas equal to or larger than 100 μm² are in a state in which two or more cells are in contact with each other and in a state in which inter-cellular contact occurs, so that it is determined to be the non-single-cells. Subsequently, the ratio of the non-single-cells having the projected area equal to or larger than 100 μm² with respect to the total number of cells is calculated (Step S66).

FIG. 11 is a drawing showing the change of the ratio of the non-single-cells at the culture times in the respective cultures (×0.5 to ×5.0) having different concentrations of the inoculated cells. FIG. 12 is a drawing showing the change of ratio of the non-single-cells at the culture times in the cultures (A to F) different in samples.

From FIG. 11 and FIG. 12, it was found that the increasing rate of the non-single-cells increases with increase in the concentration of the inoculated cells in the cultures (×0.5 to ×5.0) having different concentrations of the inoculated cells. It seems to be because the frequency of inter-cellular contact is increased with increase in number of cells per culture area, and hence positive formation of the cell aggregate was performed. In the cultures (A to F) for the six samples, it is seen that the initial ratio of the non-single-cells and the increasing rate varies from sample to sample.

An attempt was made to evaluate the proliferation potential for the cultures on the basis of the cell aggregate forming behavior. From the change of ratio of the non-single-cells with time shown in FIG. 11 and FIG. 12, the increasing rate of the non-single-cells between 24 hours to 72 hours after having initiated the culture in the respective cultures are calculated (Step S67) to inspect the correlation with respect to the minimum doubling time (a step of calculating the correlation coefficient). The result is shown in FIG. 8. The correlation coefficient between the minimum doubling time and the increasing rate of the non-single-cells was −0.964, which was a very high correlation. It indicates that the higher increasing rate of the inter-cells contact the culture has, the shorter the doubling time becomes and the higher the proliferation potential becomes. The calculated correlation coefficient may be compared with a reference value which is set in advance to select the one which is equal to or larger than the reference value (which satisfies the reference value). The relational expression is calculated by the least square method or the like from the increasing rate of the non-single-cells calculated from FIG. 11 and FIG. 12 and the minimum doubling time obtained in FIG. 10 (Step S68, a step of calculating a relational expression). The relational expression is expressed by a linear equation shown in (2) relating to the increasing rate $V_a$ and the minimum doubling time $t_d$ of the non-single-cells. The step of calculating the correlation coefficient and the step of calculating the relational expression are executed by the computer 30 as means for calculating correlation coefficients and means for calculating a relational expression.

$$t_d = c \times V_a + d \quad (2)$$

where c and d are coefficients calculated by the least square method. The minimum doubling time $t_d$ is calculated by substituting the increasing rate of the non-single-cells $V_a$ as the evaluation parameter into the linear equation of (2).

In this manner, the relational expression for estimating the minimum doubling time from the increasing rate of the non-single-cells is calculated, and the calculated relational expression is stored in the computer 30, which is used in a processing for estimating the minimum doubling time.

As described above, according to the cell culture evaluation system, the cell culture evaluation method, and the cell culture evaluation program according to the present invention, the timing of initiation of the proliferation of the inoculated cells can be estimated by estimating and evaluating the lag time, so that the cells whose proliferation potential is remarkably lowered may be determined, and hence whether or not the culture is to be continued may be determined.

According to the cell culture evaluation system, the cell culture evaluation method, and the cell culture evaluation program according to the present invention, by estimating and evaluating the minimum doubling time, the proliferation potential of the cells in question can be estimated, so that the timing to add the culture medium according, to the proliferation of the cells or the timing to change the culture vessel or the like can be estimated. Therefore, the scheduling of the culture is enabled.

When the lag time or the minimum doubling time of the estimated and evaluated culture system is too long, the corrective action corresponding thereto can be performed quickly.

According to the cell culture evaluation system, the cell culture evaluation method, and the cell culture evaluation program according to the present invention, when culturing cells sampled from the patient in the customized medical treatment, the lag time and the minimum doubling time as the proliferation potential of the cells may be estimated and evaluated efficiently within a short time without destructing and invading the cells.

Although the estimation and evaluation of the lag time and the minimum doubling time as the proliferation potential of the cells has been described thus far, a step of determining whether or not the inoculated cell population is stimulated for proliferation will now be described referring to a flowchart shown in FIG. 13 as a third embodiment. If whether or not the inoculated cell population is stimulated for proliferation can be determined automatically, objective and adequate determination for transferring the cells on cell culture from the culture vessel for stimulating the same for proliferation to a vessel for proliferation for the next stage is achieved.

The determination of whether or not the inoculated cell population is stimulated for proliferation is performed firstly by acquiring the images of the cell population on culture, then extracting the non-single-cells in the images, and calculating the ratio of the non-single-cells and, more specifically, by comparing the calculated ratio of the non-single-cells with a preset threshold value (for example, the ratio of the non-single-cells is 50 to 100%).

Figure 13:
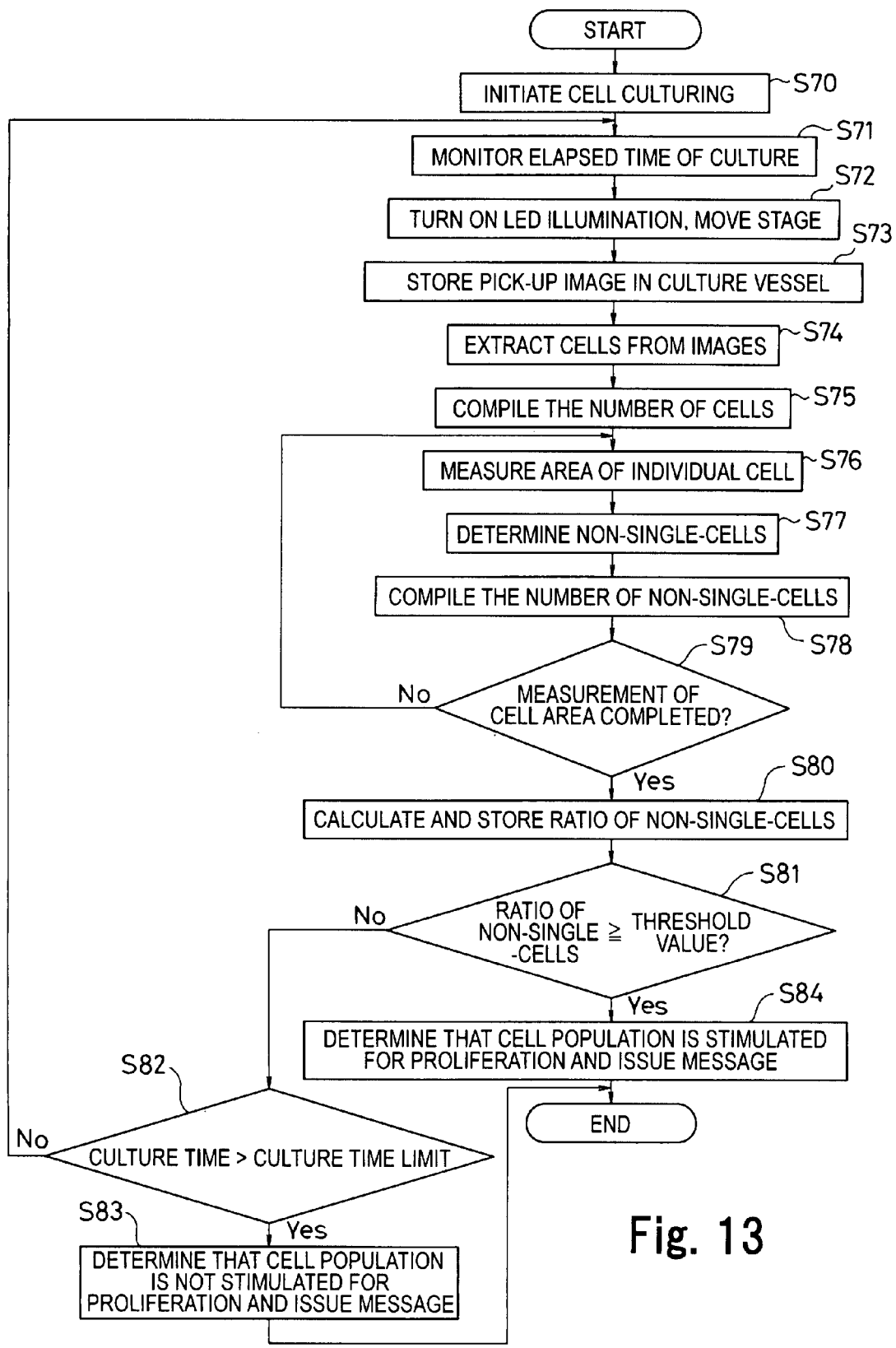
FIG. 13 is a flowchart showing a step of determining whether or not the inoculated cell population is stimulated for proliferation.

FIG. 13 is a flowchart showing a step of determining whether or not the inoculated cell population is stimulated for proliferation. Description of parts of the flowchart shown in FIG. 13 overlapped with the flowchart of the step of calculating the minimum doubling time from the increasing rate of the non-single-cells shown in FIG. 7 is simplified, and different steps will be described.

As shown in FIG. 13, as a first step, cells suspended in the culture medium are inoculated to the culture vessel 4 of which culture surface is immobilized with an antibody for stimulating the cells for proliferation and the culture is initiated (Step S70). The computer 30 shown in FIG. 1 monitors the elapsed culture time (Step S71) and outputs a control signal to the LED power source device 25 after every 12 hours from the initiation of the culture to illuminate the LED illumination device 24 positioned right above the CCD camera 21 via the culture vessel 4, moves the XYZ stage 22 and controls the stage driver 23 so that the distal end portion of the lens of the CCD camera 21 is located, for example, near the center of the bottom surface of the culture vessel 4 (Step S72). Subsequently, images are picked up by the CCD camera 21 from the bottom surface of the culture vessel 4, and image data is stored in the video memory circuit 31 in the computer 30 (Step S73).

Then, the computer 30 reads out the image data stored in the video memory circuit 31 and binarizes the same. The cells are extracted from the binarized image data (Step S74), and the number of the extracted cells is complied (Step S75). The projected areas of the extracted cells are measured (Step S76).

Subsequently, the extracted cells are discriminated between the single-cells and the non-single-cells which form the cell aggregate. Discrimination between the single-cells and the non-single-cells is done by determining those having the projected area equal to or larger than 100 μm² as the non-single-cells (Step S77). A step of discriminating the cell morphology for discriminating the single-cells and the non-single-cells is executed by the computer 30 as cell morphology discriminating means.

Subsequently, the discriminated non-single-cells are extracted and the number of the extracted non-single-cells is compiled (Step S78). Whether or not the measurement of the projected areas of all the cells is completed is checked (Step S79). After having completed the measurement of the projected areas of all the cells, the ratio of the non-single-cells with respect to the number of cells compiled in Step S75 is calculated and is stored in the memory of the computer together with the culture time from the initiation of the culture (Step S80).

Then, the computer 30 compares the calculated ratio of the non-single-cells with the threshold value of the ratio of the non-single-cells set in advance (Step S81). When the ratio of the non-single-cells is smaller than the threshold value, whether or not the culture time exceeds a preset culture time limit is checked (Step S82). When the culture time exceeds the culture time limit, it is determined that the cell population on culture is not stimulated for proliferation and a message indicating that the cell population is not stimulated for proliferation is issued on a display device or the like (Step S83). When the culture time is within the culture time limit, the procedure goes to Step S71, and the procedures from Step S72 on are executed again after 12 hours of the culture time has elapsed. The threshold value of the ratio of the non-single-cells is determined from the drawing which shows the change of ratio of the non-single-cells at the culture times in FIG. 11 or FIG. 12.

When the ratio of the non-single-cells is equal to or higher than the threshold value in the comparing process in Step S81, the computer 30 determines that the cell population on culture is stimulated for proliferation, and issues a message indicating that the stimulation of the cell population for proliferation is completed to the display device or the like. Accordingly, it is determined that the cell population has stimulated for proliferation, and the cells on cell culture can be transferred from the culture vessel for stimulating the same for proliferation to the vessel for proliferation for the next stage (Step S84).

In the step of determining whether or not the inoculated cell population is stimulated for proliferation shown in FIG. 13, the ratios of the non-single-cells for every culture time are calculated and stored in the memory, and hence the increasing rate of the non-single-cells may be calculated using the stored data, so that the minimum doubling time can also be calculated.

As described thus far, with the cell culture evaluation system, the cell culture evaluation method, and the cell culture evaluation program according to the present invention, whether or not cell population is stimulated for proliferation may be determined from the ratio of the non-single-cells, and objective and adequate determination for transferring the cells on culture for the next stage (for example, transferring the cells from the culture vessel for stimulating it for proliferation to the vessel for proliferation) is achieved.

Furthermore, when it is determined that the cell population is not stimulated for proliferation from the ratio of the non-single-cells, the process corresponding thereto can be performed quickly.

The invention claimed is:

1. A cell culture evaluation system comprising:
   a culture device for static culture in a culture vessel; and
   a measuring device configured to measure suspension cells to be cultured by the culture device, wherein the measuring device includes (i) image acquiring means configured to acquire images of the suspension cells in the culture vessel, (ii) average projected area calculating means configured to extract single-cells from image data acquired by the image acquiring means at a certain culture time, to calculate a projected area of the extracted single-cells, and to calculate an average projected area of the single-cells, and (iii) a lag time determining means configured to determine a lag time by correlating the average projected area of the extracted single-cells with lag times and average projected areas of single cells from a previously-cultured sample,
   wherein the culture device comprise a culture vessel stage configured to have the culture vessel mounted thereon,
   wherein the measuring device includes an illumination device positioned to illuminate from above the culture vessel mounted on the culture vessel stage,
   wherein the image acquiring means of the measuring device is positioned to acquire the images of the suspension cells in the culture vessel from below the culture vessel, such that the culture vessel stage is between the illumination device and the image acquiring means, wherein the measuring device determines a lag time of the cultured suspension cells from the average projected area of the single-cells calculated by the average projected area calculating means, and wherein the measuring device acquires the images, calculates the average projected area, and determines the lag time, when a preset time has elapsed from initiation of the culture in the culture vessel.

2. The cell culture evaluation system according to claim 1, wherein, to correlate the average projected area of the single-cells, the lag time determining means uses a relational expression between the average projected area of the single-cells at the culture time and the lag time.

3. The cell culture evaluation system according to claim 1, wherein the average projected area of the single-cells used by the lag time determining means is employed as a parameter for evaluating a proliferation potential of the cell population.

4. The cell culture evaluation system according to claim 2, further comprising:
means for calculating lag times from proliferation profiles of suspension cells in at least two samples;
means for calculating the average projected areas of single-cells at culture times of the respective samples;
means for calculating correlation coefficients between the average projected areas at respective culture times and the lag times of the cells of the respective samples; and
means for calculating, as the relational expression used by the measuring device, a relational expression between the average projected area corresponding to the culture time having a correlation coefficient equal to or higher than a reference value and the lag time.

5. A cell culture evaluation system comprising:
a culture device for static culture in a culture vessel; and
a measuring device configured to measure suspension cells after culturing the cells by the culture device has started, wherein the measuring device includes (i) image acquiring means for acquiring images of a cell population in the culture vessel, (ii) means for extracting cells from the images, compiling a number of the extracted cells, and measuring projected areas of the extracted cells, (iii) means for discriminating single-cells and non-single-cells which form cell aggregates among the extracted cells, (iv) means for extracting and compiling a number of the non-single-cells, (v) means for calculating a ratio of the non-single-cells to a number of cells in the cell population, (vi) means for calculating an increasing rate of the non-single-cells from the ratio of the non-single-cells calculated by the means for calculating the ratio of the non-single-cells, and (vii) a minimum doubling time determination means configured to determine the minimum doubling time of the suspension cells from the increasing rate of the non-single-cells calculated by the means for calculating the increasing rate of the non-single-cells,
wherein the culture device comprise a culture vessel stage configured to have the culture vessel mounted thereon,
wherein the measuring device includes an illumination device positioned to illuminate from above the culture vessel mounted on the culture vessel stage,
wherein the image acquiring means of the measuring device is positioned to acquire the images of the suspension cells in the culture vessel from below the culture vessel, such that the culture vessel stage is between the illumination device and the image acquiring means, and wherein the measuring device determines a minimum doubling time of cultured cells from the increasing rate of the non-single-cells calculated by the means for calculating the increasing rate of the non-single-cells.

6. The cell culture evaluation system according to claim 5, wherein the measuring device calculates the minimum doubling time of the cultured cells from a relational expression between the increasing rate of the non-single-cells in the cell population at a culture time and the minimum doubling time of the cell population.

7. The cell culture evaluation system according to claim 5, wherein the increasing rate of the non-single-cells used by the measuring device is employed as a parameter for evaluating a proliferation potential of the cell population.

8. The cell culture evaluation system according to claim 6, further comprising:
means for calculating the increasing rate of the non-single-cells in at least two samples;
means for calculating doubling times of the cells from the increasing rates of the non-single-cells in the respective samples;
means for employing a shortest time from among the calculated doubling times of the cells as a minimum doubling time;
means for calculating a correlation coefficient between the increasing rate of the non-single-cells in a predetermined culture time and the minimum doubling time; and
means for calculating, as the relational expression used by the measuring device, a relational expression between the increasing rate of the non-single-cells having a correlation coefficient equal to or higher than a reference value and the minimum doubling time.

9. A cell culture evaluation system comprising:
a culture device for static culture in a culture vessel; and
a measuring device for measuring suspension cells to be cultured by the culture device, wherein the measuring device includes (i) image acquiring means for acquiring images of a cell population to be cultured statically in the culture vessel, (ii) extracting means for extracting non-single-cells from the images acquired by the image acquiring means, (iii) means for calculating a ratio of the non-single-cells to a number of cells in a cell population from the non-single-cells extracted by the extracting means, and (iv) means for determining whether or not the cell population is stimulated for proliferation from the ratio of the non-single-cells calculated by the means for calculating the ratio of the non-single-cells to the number of cells in the cell population, by determining that the cell population is stimulated for proliferation when the ratio of the non-single-cells is higher than a pre-calculated threshold value,
wherein the culture device comprise a culture vessel stage configured to have the culture vessel mounted thereon,
wherein the measuring device includes an illumination device positioned to illuminate from above the culture vessel mounted on the culture vessel stage, and
wherein the image acquiring means of the measuring device is positioned to acquire the images of the suspension cells in the culture vessel from below the culture vessel, such that the culture vessel stage is between the illumination device and the image acquiring means.

\* \* \* \* \*